Figure 1A:
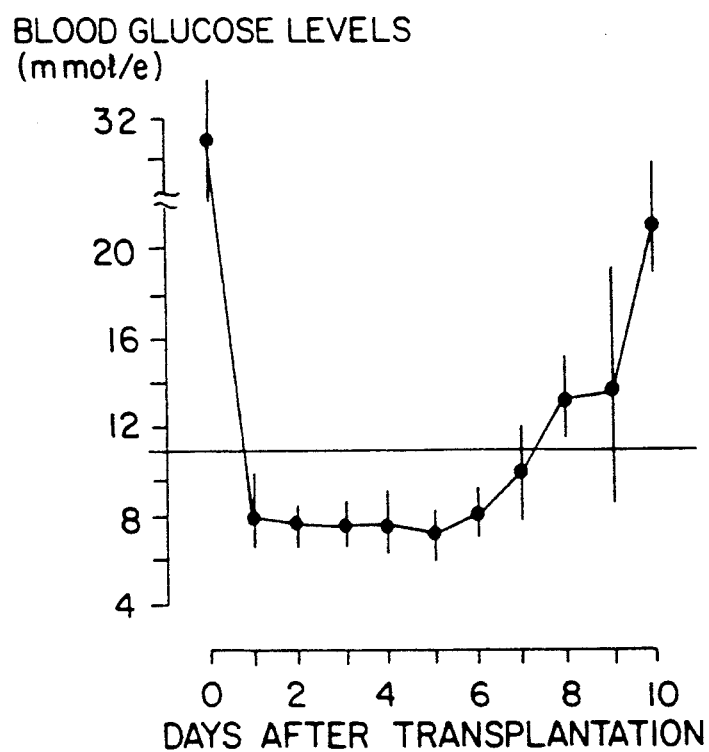

United States Patent [19]

Braganza et al.

[11] Patent Number: 5,196,402
[45] Date of Patent: Mar. 23, 1993

[54] S-ADENOSYL-METHIONINE IN THE TREATMENT OF PANCREATITIS AND OF THE IMMUNO REJECTION IN THE PANCREAS TRANSPLANT

[75] Inventors: Joan M. Braganza, Sale; Ian V. Hutchinson, Stockport, both of United Kingdom

[73] Assignee: Bioresearch S.p.A., Milan, Italy

[21] Appl. No.: 573,211

[22] PCT Filed: Jan. 10, 1990

[86] PCT No.: PCT/EP90/00048
§ 371 Date: Aug. 15, 1990
§ 102(e) Date: Aug. 15, 1990

[87] PCT Pub. No.: WO90/07928
PCT Pub. Date: Jul. 26, 1990

[30] Foreign Application Priority Data

Jan. 14, 1989 [GB] United Kingdom ............... 8900812

[51] Int. Cl.$^5$ ..................... A61K 31/16; A61K 31/70
[52] U.S. Cl. ......................................... 514/9; 514/46; 530/317; 536/27.31
[58] Field of Search ............... 514/45, 46, 11; 536/24, 536/26; 530/317, 321; 544/177

[56] References Cited

FOREIGN PATENT DOCUMENTS 136464 8/1984 European Pat. Off. .
191133 8/1985 European Pat. Off. .

OTHER PUBLICATIONS

Loeser et al., "Inhibitory Effect of Acute and Chronic Application of Cyclosporin on Ornithinearboxylase (ODC), S-Adenosylmethionine Decarboxylase (SAM-DC), Polyamines and Trophic Parameters in Camostate-Induced Pancreatic Growth in Rats", Abstract No. 98, XXI Meeting of the European Pancreatic Club, Glasgow, Scotland, Sep. 20-23, 1989, in *Digestion*, 43(3), 160 (1989).

Squifflet et al., "Six human pancreas transplants: results and perioperative management", *Acta Anesthesiologica Belgica*, 37(2), 107-112 (1986).

Grillo et al., "S-Adenosylmethionine Decarboxylase in Liver, Heart and Pancreas of Pyridoxine-deficient Chickens", *Ital. J. Biochem.*, 26(5), 342-346 (1977).

Dyer et al., "Evidence for Altered Methionine Methyl-Group Utilization in the Diabetic Rat's Brain", *Neurochemical Research*, 13(6), 517-523 (1988).

Vandenbark et al., "Inhibition of Lymphocyte Transformation by a Naturally Occurring Metabolite: 5'-methylthioadenosine", *Cell Immunol.*, 49(1), 26-33 (1980).

Budavari et al. (eds.), "The Merck Index, 11th Ed.", Merck and Co., Rahway, N.J., 1989, see p. 26, entry No. 146.

DiPadova et al., "Inhibition of Lymphocyte Function by a Naturally Occurring Nucleoside: 5'-methylthioadenosine (MTA)", *Int. J. Immunopharmacology*, 7(2), 193-198 (1985).

Cavallo-Perin et al., "The Pharmacological Effect of S-Adenosyl-Methionine (SAMe) on Glucose Metabolism in Normal Subjects and Diabetic Patients", *Current Therapeutic Research*, 26(6), 982-989 (1979).

Loser et al., "Dose-dependant Inhibition of the Induction of Pancreatic Ornithine Decarboxylase and Polyamines in Rats by Cyclosporine A", *Eur. J. Clin. Invest.*, 19, A42 (1989).

The Merck Manual, (1987), pp. 322-329, 335.

*Primary Examiner*—John W. Rollins
*Assistant Examiner*—L. Eric Crane
*Attorney, Agent, or Firm*—Birch, Stewart, Kolasch & Birch

[57] ABSTRACT

Therapeutic composition comprising S-adenosyl-methionine useful in the treatment of pancreatitis and as synergistic agent of cyclosporin in the prevention of the graft rejection in pancreas transplant.

4 Claims, 4 Drawing Sheets

S-ADENOSYL-METHIONINE IN THE TREATMENT OF PANCREATITIS AND OF THE IMMUNO REJECTION IN THE PANCREAS TRANSPLANT

This invention relates to therapeutic compositions and method for the treatment of pancreatitis and in particular for the immuno-suppressive treatment of the graft rejection after pancreas transplant.

Pancreatitis is a painful condition which may resolve spontaneously or may kill the sufferer from haemorrhagic necrosis or cause recurrent pain from chronic destruction of the gland. There is no specific treatment for it.

Transplantation of organs or tissue from a donor to a recipient is carried out frequently as a means for replacing failing or diseased organs or tissue by healthy alternatives from another host (allogeneic graft), but this procedure suffers from the danger that the transplanted or grafted organ or tissue will be rejected by the recipient, unless the donor and the recipient are genetically identical (syngeneic graft). Such rejection can be reduced by use of various known drugs which have an immuno-suppressive effect—i.e. they reduce the activity of the mechanism by which the body rejects the implanted material. The mechanism is not fully understood, and there is great need for new treatment agents and methods which can reduce the rejection rate more effectively.

We now have found, surprisingly, that the compound S-adenosylmethionine has valuable properties in the treatment of pancreatitis and as synergizing agent of the immuno-suppressive effect of cyclosporine in combating graft rejection after the pancreas transplant.

The subject to be treated by the method of the invention may be human or animal. We find that the method is applicable to all forms of pancreatitis but especially to the treatment and/or prevention of haemorrhagic pancreatic necrosis and also especially to the treatment of rejection in genetically high responder recipients of transplanted pancreas which is particularly susceptible to inflammatory damage.

The S-adenosyl-methionine is a known compound, described in the literature and available commercially (for example from Bioresearch Spa, Milan, Italy and from Sigma Chemical Company).

The L-enantiomer, S-adenosyl-L-methionine is preferred.

As the compound forms a variety of salts derived from various acids and some of these salts (for example the chloride and, to a lesser degree, the iodide) can be unstable, we prefer to use the compound in the form of a salt which is relatively stable at ambient temperatures, for example the p-toluenesulphonate (available from Sigma Chemical Company, Catalogue No. A.2408).

According to the invention we also provide pharmaceutical compositions, useful for the treatment of inflammatory or graft-rejection conditions, comprising S-adenosyl-methionine as active ingredient.

The S-adenosyl-methionine may be administered in the form of conventional compositions, which may be solutions, dispersions or suspensions in conventional diluent or carrier media appropriate for the systemic introduction of the compound into the body of the recipient to be treated. Thus it may be administered in any appropriate conventional medium compatible with it, for example 0.2M disodium phosphate.

Administration to the body to be treated or protected may be by injection or infusion using conventional techniques, for example intramuscularly, intravenously or intraperitoneally, or by oral means, or by any combination of such techniques. As it appears that the compound can be gradually destroyed in the body, it is highly desirable to maintain a continuing supply of the compound by following up with administration of further doses by the preferred technique. Thus, for example, it is conveniently administered on a "three times per day" basis.

The dosage level may vary according to the severity of the condition and/or the particular subject being treated, but is usually in the range 10 mg to 2.5 g per kg body weight, and preferably in the range 25 mg to 1.0 g per kg body weight. Administration is conveniently effected as a solution in a pharmaceutically acceptable solvent (e.g. water) at a concentration of the order of 25 mg/ml. Higher or lower proportions and dosages may be used if desired, and likewise higher or lower concentrations in compositions administered may be used if desired.

The treatments and compositions of the invention may comprise known adjuvants and other active ingredients, and such active ingredients may be administered simultaneously or sequentially, as desired. Examples of such active ingredients include antioxidants and their precursors (for example N-acetyl-cysteine), anti-inflammatory agents (for example 5-amino-salicylic acid), and combinations thereof, provided these are compatible with the S-adenosyl-methionine.

It has been surprisingly found that the administration of S-adenosyl-methionine in combination with the administration of cyclosporin, optionally through the administration of only one therapeutic composition containing both active principles, affords extraordinary success in combating the immuno rejection of hosts to implanted pancreas. Optimal results are obtained through administration of S-adenosyl-methionine at dosage of 25 mg/kg body weight in combination with cyclosporine at dosage of 20 mg/kg body weight. With the term cyclosporin we mean all the cyclosporins known as immunosuppressive agent.

Most pancreas transplants show histological signs of pancreatitis. Such damage is a consequence of a non-specific response of the exocrine pancreas to a variety of injurious agents and, in the case of the transplanted organ, can be triggered by the immune response to foreign alloantigens. Two major forms of pancreatitis are distinguishable by histological examination, an oedematous form which appears to precede a condition described as haemorrhagic pancreatic necrosis. The response may stop short at a stage of interstitial oedema with raised serum amylase levels due to acinar cell damage or may progress inexorably to the necrotic form with death from multi-system organ failure, as in 20% of human cases of acute pancreatitis. There is no satisfactory treatment, partly because the pathogenic process is poorly understood. However, the stereotyped response to injurious agents suggests that the basic mechanism of tissue damage is the same whatever the putative aetiological factor may be.

The experimental tests hereafter reported show that treatment of allograft recipients with cyclosporin alone blunted the immune response but did not prevent pancreatitis so that animals died while normoglycaemic with a median survival time of 11 days. The major evidence of tissue damage was histological. Treatment with SAMe alone reduced interstitial oedema and animals lived long enough to develop hyperglycaemia because of rejection of the graft islets; the combination of the two active principles controlled both problems thereby ensuring long-term survival of the animals.

We chose to transplant pancreaticoduodenal grafts from PVG/c (RT1$^c$) to PVG.RT1$^u$ rats because all organ transplants are rejected acutely and with particular vigour in this "high responder" strain combination. The results of the tests are summarized in table 1. The following comments can be pointed out.

Figure 1C:
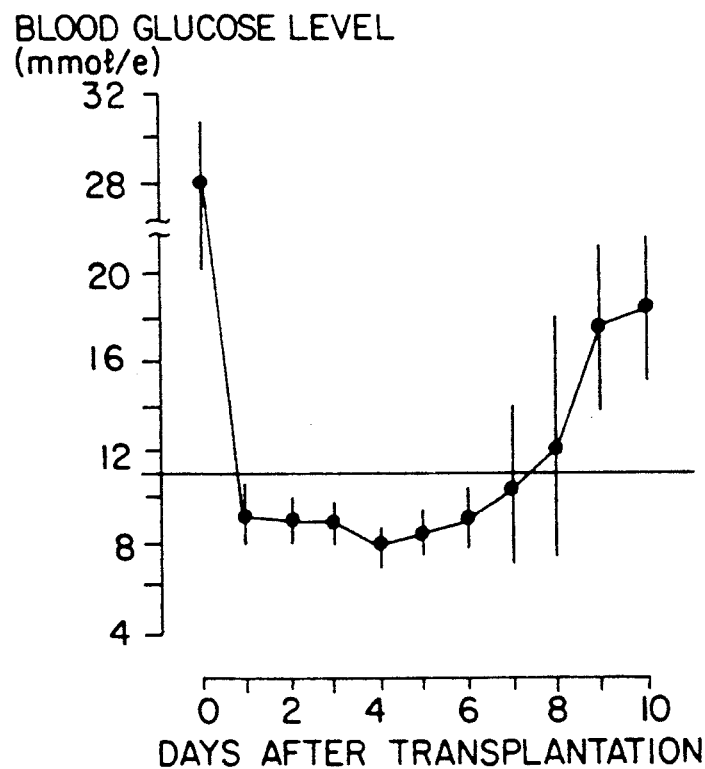
Figure 1B:
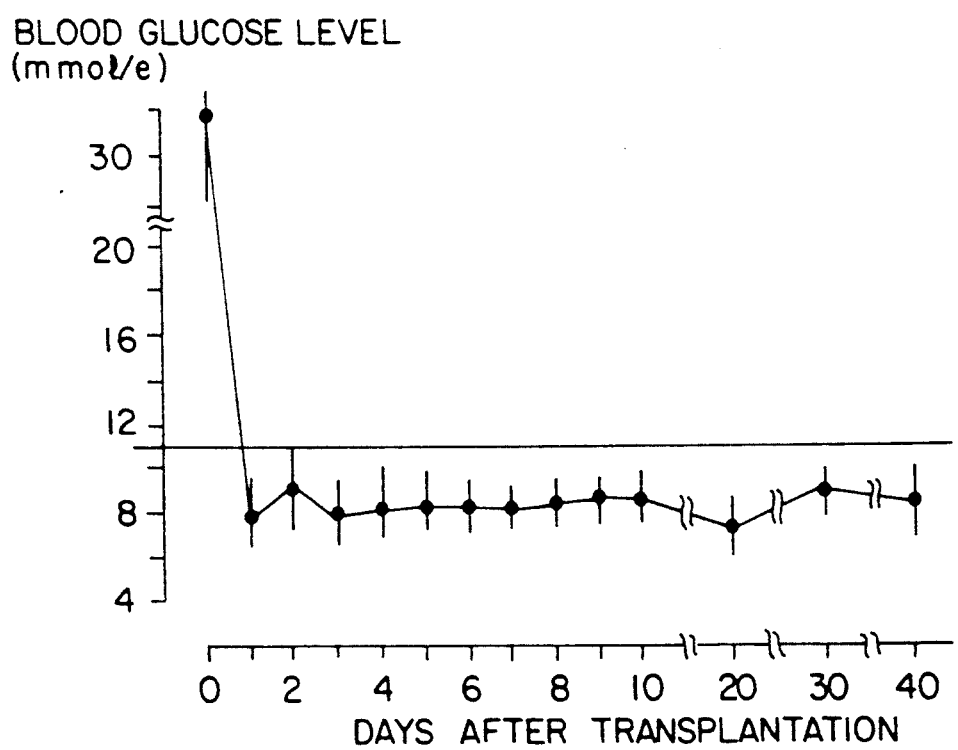
Figure 1D:
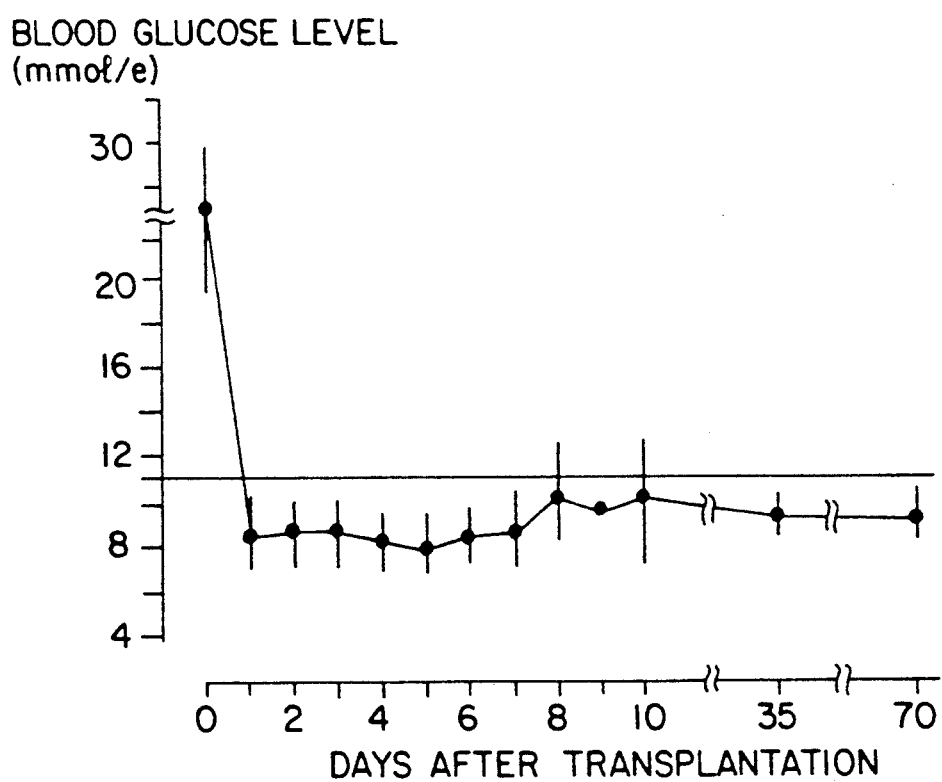

Treatment of pancreas recipients with Cyclosporin A at 20 mg/kg had little effect on their survival; 6/8 rats died normoglycaemic within the 14 day treatment period (table 1, group 3 and FIG. 1$b$). Gross changes included massive oedema and haemorrhage throughout the graft at the time of death. Histologically, the onset of all but mild oedema (Table 2, group c) was delayed until day 5 after grafting. Cellular infiltration (Table 3, group c) was reduced, too, with a mild infiltrate from day 2–5 consisting initially of polymorphs, followed by macrophages then lymphocytes. On day 6–7 the oedema increased and polymorphs returned to the infiltrate which was severe by day 7. Acinar cell loss was gradual from day 4 but was severe on day 7. Islets remained normal throughout consistent with normoglycaemia at death (FIG. 1$b$). Induction of expression of Class I MHC antigens on islets and acinar cells was reduced compared with untreated grafts but increased with the T cell infiltrate from day 4 and were very strongly expressed by day 7.

Figure 2A:
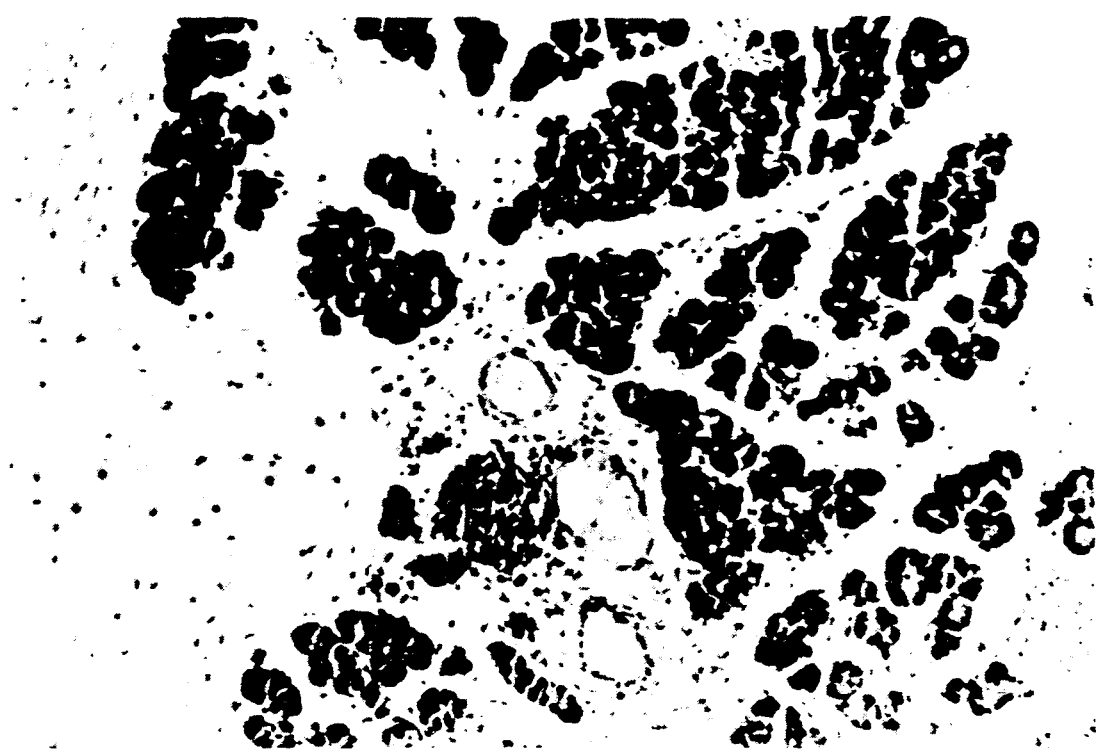
Figure 2B:
Figure 2C:
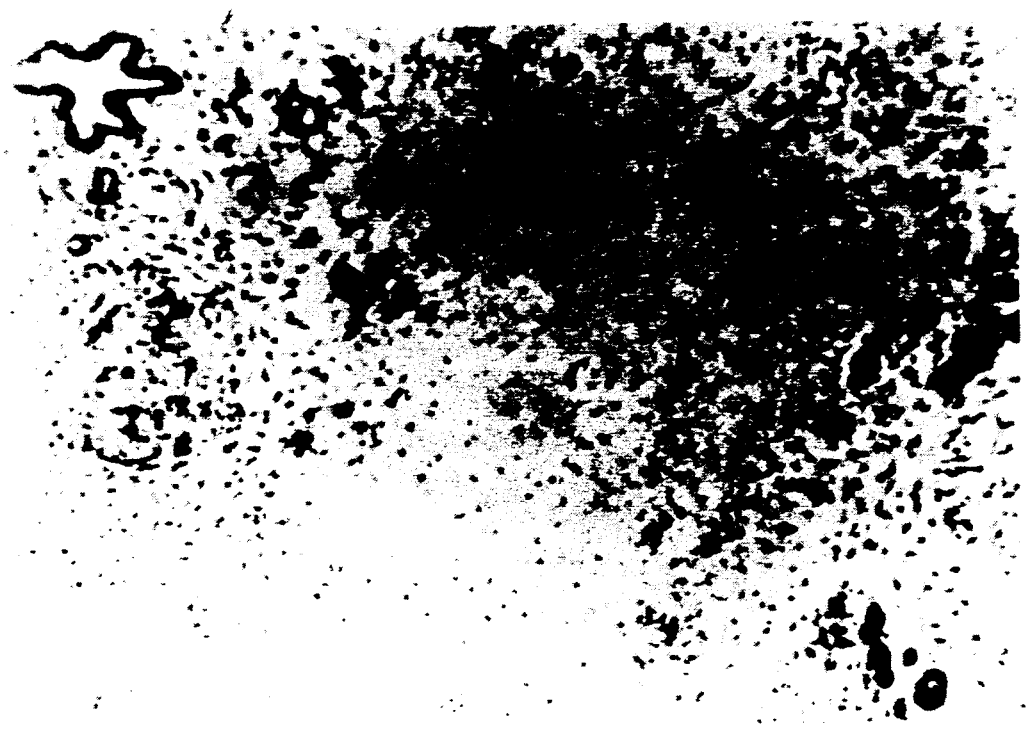
Figure 2D:
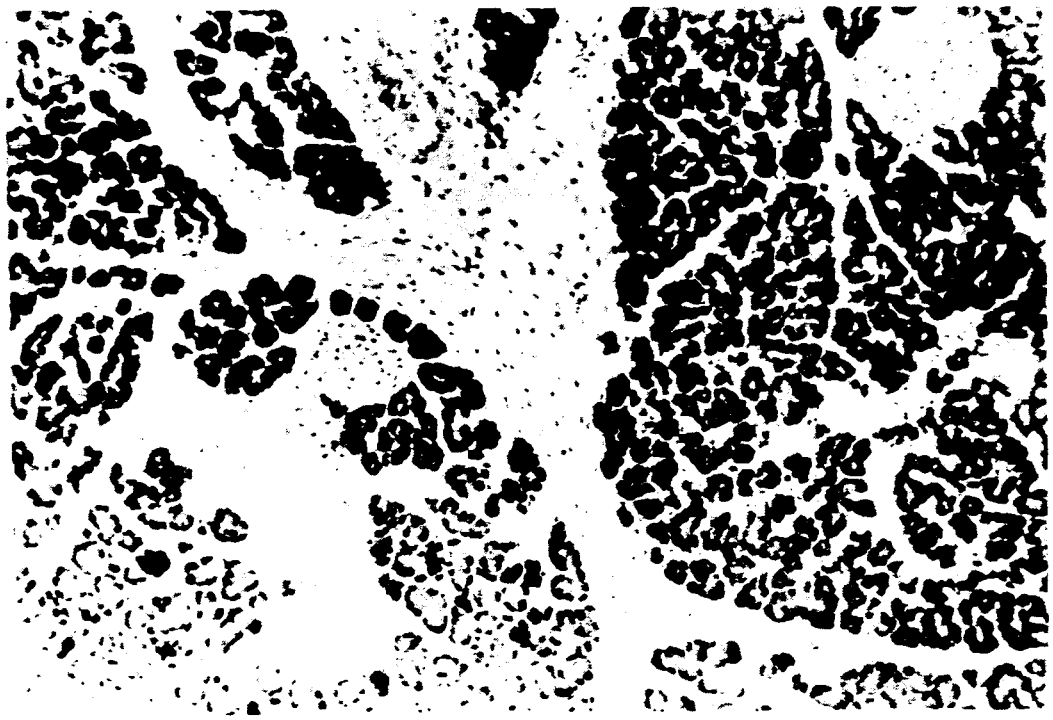

It would appear that SAMe is not an immunosuppressive agent in its own right since rejection occurred despite its administration. It does have some anti-inflammatory activity in this model because it reduced graft oedema in the first 5 days (Table 2, group d) but it did not alter infiltration (Table 3, group d) and had little discernable effect (at the dose given) on the rejection-associated pancreatitis driven by the presence of activated T cells (Table 1, group 4 and FIG. 2$c$).

In the final group, when recipients were treated with both Cyclosporin A and SAMe, 7 out of 8 went on to survive for more than 100 days (table 1, group 5) with normoglycaemia (FIG. 1$d$). There was mild oedema on day 4, but this resolved by day 8 (Table 2, group e). The infiltrate (Table 3, group e) was always mild, with fewer polymorphs which were not apparent by day 8 and lymphocytes which had vanished by day 12 (FIG. 2$d$). Ducts, acinar cells and islets were perfect throughout the first two weeks at least, although there was a little induction of MHC antigens on these structures.

The same results of group 5 have been obtained by giving a single daily dose of 100 mg/kg (body weight) of SAMe+20 mg/kg of cyclosporin A. SAMe was administered for 10 days by i.m. injection starting on the day of grafting and cyclosporine was administered for a period of 14 days.

TABLE 1

Survival of rat pancreaticoduodenal allografts[a] after treatment with Cyclosporin A and S-adenosyl methionine

| Group | Treatment | n | Graft Survival (days)[b] | Median Survival time (days) |
|---|---|---|---|---|
| 1 | None | 10 | 7(× 2),8(× 6),9,10 | 8 |
| 2 | Carrier[c] | 4 | 8,8,10 | 9 |
| 3 | CsA (20 mg/kg)[d] | 8 | 8,10(× 2),11(× 3) 100(× 2) | 11 |
| 4 | SAMe (25 mg/Kg)[e] | 7 | 7,8,8,9(× 3),10 | 9 |
| 5 | SAMe (25 mg/Kg) plus CsA (20 mg/Kg)[f] | 8 | 31,>100(× 7) | >100 (p = 0.007)[g] |

Notes

[a]Transplants were performed in the PVG/c (RT1$^c$) to PVG.RT1$^u$ donor-recipient combination. Recipients were rendered diabetic by treatment with streptozotocin 1 day before transplantation.

[b]Graft rejection was defined by persistent blood glucose levels > 11 mM/l.

[c]Carrier = olive oil (1 ml/kg/day by mouth for 14 days) plus 0.2M Na$_2$HPO$_4$ solution, pH 5,0 (1 ml/kg/day three times daily by intramuscular injection for 10 days).

[d]CsA = Cyclosporin A at 20 mg/ml in olive oil, given orally at 1 ml/kg/day for 14 days beginning immediately post-operatively.

[e]SAMe S-adenosyl methionine dissolved in 0.2M Na$_2$HPO$_4$ at 25 mg/ml and injected im at 1 ml/kg 3 times daily at 8 hour intervals for 10 days beginning immediately after transplantation.

[f]Combined treatment as in groups 3 and 4.

[g]Statistical significance of difference between groups 3 and 5 using the Mann-Whitney (Rank Sum) non-parametric method.

TABLE 2

Histological findings (oedema) in rat pancreaticoduodenal allografts treated with Cyclosporin A and S-adenosylmethionine compared with syngeneic and allogeneic untreated grafts.

| GROUP | DAYS AFTER TRANSPLANTATION | | | | | |
|---|---|---|---|---|---|---|
| | 2 | 4 | 6 | 8 | 10 | 12 |
| A. syngeneic (untreated) | ± | ++ | + | ± | ± | − |
| B. allogeneic (untreated) | +++ | +++ | +++ | ++ | · | · |
| C. allogeneic (CsA alone) | ± | ++ | +++ | ++++ | · | |
| D. allogeneic (SAMe alone) | + | ++ | ++ | ++++ | · | · |
| E. allogeneic (CsA + SAMe) | ± | + | + | + | + | ± |

Legend:
± very mild interstitial oedema
+ mild interstitial oedema
++ clear separation of acinar lobules
+++ moderate oedema
++++ severe oedema
· no identifiable acinar tissue

TABLE 3

Histological findings (infiltration) in rat pancreaticoduodenal allografts treated with Cyclosporin A and S-adenosylmethionine compared with syngeneic and allogeneic untreated grafts.

| GROUP | DAYS AFTER TRANSPLANTATION | | | | | |
|---|---|---|---|---|---|---|
| | 2 | 4 | 6 | 8 | 10 | 12 |
| A. syngeneic (untreated) | ++ (P) | +++ (P + M) | ++ (M>P) | + (M>L) | ± (M + L) | ± (M + L) |
| B. allogeneic (untreated) | +++ (P) | +++ (M + L) | +++ (M + L) | ++ (P>M + L) | · | · |
| C. allogeneic (CsA alone) | ++ (P) | + (M + L>P) | ++ (M>L) | + (M + L) | · | · |
| D. allogeneic (SAMe alone) | + (P) | ++ (M) | +++ (P,M + L) | ++++ (P>M + L) | · | · |
| E. allogeneic (CsA + SAMe) | + (P) | + (M + L) | ± (M + L) | ± (M + L) | | ± (M + L) |

Legend:
± Minimal infiltrate to ++++ severe/dense infiltrate
· no identifiable acinar tissue
Parentheses indicate constitution and proportions of cells in the infiltrate:
P = Polymorphonuclear cells
M = monocytes/macrophages
L = lymphocytes/plasma cells

LEGENDS TO FIGURES (BRIEF DESCRIPTIONS OF THE FIGURES)

FIG. 1 Blood glucose levels in pancreaticoduodenal transplant recipients

Panel a) pooled data for groups 1 and 2 (no treatment and carrier treatment, respectively).

Panel b) data for group 3 recipients treated with CsA (20 mg/kg/day) alone.

Panel c) levels in recipients from group 4 given SAMe (25 mg/kg/day) alone.

Panel d) data for grafted rats in group 5 given both Csa and SAMe.

FIG. 2 Histological appearance of grafted tissues from pancreaticoduodenal transplant recipients a) Syngeneic transplantation at 8 days after grafting. H+E (×180).

Mild oedema separating the lobules of acinar tissue. Very mild infiltration with macrophages and some lymphocytes. Acinar cells are viable and well granulated. Islets are also found in abundance.

b) Untreated allograft at 7 days after grafting. H+E (×180).

Extensive necrotic damage to the left and residual exocrine ductal tissue to the right. In between is a "pallisade" of neutrophils. The area to the right is heavily infiltrated with polymorphs and macrophages and there is evidence of extensive haemorrhage.

c) SAMe-treated allograft at 7 days after grafting. H+E (×180).

Severe necrosis of pancreatic acinar tissue wit residual ductal structure, and an inflammatory cell infiltrate consisting of polymorphs and macrophages with some lymphocytes. Viable islets are visible in such graft; there is a distorted but otherwise intact islet to the left.

d) Allograft treated with CsA and SAMe at 8 days after transplantation. H+E (×180).

Normal acinar tissue showing very mild oedema and minimal infiltration.

The principle cells are macrophages, although they are few, Normal islets can be seen throughout the tissue, in this section in the centre and at the bottom left corner.

We claim:

1. A therapeutic method for treating pancreatitis in a patient in need thereof comprising administering a therapeutically effective amount of SAMe or a pharmaceutically acceptable salt thereof.

2. A therapeutic method, according to claim 1, wherein SAMe or a pharmaceutically acceptable salt thereof is administered in an amount ranging from 10 to 2500 mg/kg.

3. A therapeutic method for treating pancreatitis and for reducing graft rejection, both occurring after pancreas transplant in a patient in need thereof comprising administering a therapeutically effective amount of SAMe or pharmaceutically acceptable salts thereof, in combination with a therapeutically effective amount of cyclosporin.

4. The therapeutic method, according to claim 3, wherein SAMe is administered at a daily dosage of about 25 mg/kg body weight and cyclosporin is administered at a dosage of about 20 mg/kg.

* * * * *